United States Patent [19]

Thuillier et al.

[11] 4,148,915

[45] Apr. 10, 1979

[54] BIS(2-PHENOXYALKANE CARBOXYLIC ACIDS) AND DERIVATIVES THEREOF AND THEIR USE AS MEDICAMENTS

[75] Inventors: Germaine Thuillier, Paris; Sylviane S. J. Mignonac; Pierre A. R. Bessin, both of Chilly-Mazarin, all of France

[73] Assignee: Albert Rolland, S.A., Paris, France

[21] Appl. No.: 739,963

[22] Filed: Nov. 8, 1976

[30] Foreign Application Priority Data

Nov. 14, 1975 [FR] France .................. 75 34825

[51] Int. Cl.$^2$ .................. C07C 149/40; C07C 69/84; A61K 31/215

[52] U.S. Cl. .................. 424/308; 560/9; 560/11; 560/61; 560/62; 562/426; 562/429; 562/471; 562/472; 424/317

[58] Field of Search .................. 260/470, 473 G, 516, 260/520 B; 424/308; 560/9, 11, 61, 62; 562/426, 429, 471, 472

[56] References Cited

U.S. PATENT DOCUMENTS

| 3,169,144 | 2/1965 | Cavallini | 260/473 G |
|---|---|---|---|
| 3,470,235 | 9/1969 | Jackson | 260/473 G |
| 3,686,271 | 8/1972 | Lefon | 260/520 C |
| 3,784,697 | 1/1974 | Nahm | 424/308 |

FOREIGN PATENT DOCUMENTS 2224649 12/1972 Fed. Rep. of Germany.
856388 12/1960 United Kingdom.
1165334 9/1969 United Kingdom.

OTHER PUBLICATIONS

Tyler, J. Appl. Chem., 9, pp. 594–599 (1959).
Okon, Chem. Abst., 49:918f (1955).
Pfleger, Chem. Abst., 44:5837g.
Kolesnikov, Chem. Abst., 74:53244s (1971).

Primary Examiner—James O. Thomas, Jr.
Assistant Examiner—Michael Shippen
Attorney, Agent, or Firm—Stevens, Davis, Miller & Mosher

[57] ABSTRACT

Bis (2-phenoxyalkane carboxylic acids) and their esters and salts, as well as a method for their preparation. These compounds are useful for the treatment of hyperlipemia and arteriosclerosis.

18 Claims, No Drawings

BIS(2-PHENOXYALKANE CARBOXYLIC ACIDS) AND DERIVATIVES THEREOF AND THEIR USE AS MEDICAMENTS

This invention relates to bis(2-phenoxyalkane carboxylic acids) and their esters and pharmaceutically acceptable salts which are useful in the treatment of hyperlipemia and arteriosclerosis, and to a process for their preparation, to methods of treatment with pharmaceutically effective amounts thereof and to pharmaceutical compositions containing such compounds as essential ingredients.

Clofibrate (ethyl 2-p-chlorophenoxy-2 methyl propionate) is already known as a hypolipemic and hypocholesteremic agent.

Other hypolipemic and hypocholesteremic agents are derivatives of 4-phenoxy phenoxyalkane carboxylic acids, described in French Pat. No. 72. 26568 (issued under No. 2 147 138; priority 23rd July, 1971, Federal Republic of Germany (Hoechst)).

This invention relates to novel derivatives of bis(2-phenoxyalkane carboxylic acids) of the formula

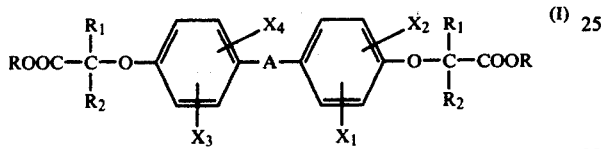

in which
R represents a hydrogen atom or an alkyl group having from 1 to 5 carbon atoms,
$R_1$ represents a hydrogen atom or an alkyl group having from 1 to 3 carbon atoms,
$R_2$ represents a hydrogen atom or an alkyl group having from 1 to 12 carbon atoms,
A represents O. S, SO or $SO_2$, and
$X_1$, $X_2$, $X_3$ and $X_4$, any two or more of which may be the same or different, each represents a hydrogen or halogen atom or an alkyl group having from 1 to 3 carbon atoms.

The present invention also relates to salts of compounds of the formula I in which R represents a hydrogen atoms, especially pharmaceutically acceptable salts of such compounds.

Alkyl groups in a compound of the general formula I or in the salts thereof are unbranched or branched. There may especially be mentioned compounds in which A represents an oxygen atom and in which R represents a hydrogen atom or an alkyl group having from 1 to 3 carbon atoms, in which $R_1$ represents a hydrogen atom or a methyl group and in which $R_2$ represents a hydrogen atom or a straight chain alkyl group, especially one having from 1 to 10 carbon atoms. Substituents represented by $X_1$, $X_2$, $X_3$ and $X_4$ may be in any of the free positions on the aromatic rings. For example, there may be one or two halogen substituents on the same ring meta to the group represented by A. Preferably, $X_1$ and $X_3$ have the same meaning and are in the same position with respect to A, and $X_2$ and $X_4$ have the same meaning and are in the same position with respect to A. There may especially be mentioned 4,4'-oxy di(ethyl 2-phenoxy octanoate), 4,4'-oxy di(2-phenoxy octanoic acid), and its salts, and 4,4'-thio di(2-phenoxy octanoic acid), its esters and its salts.

A salt may be an alkali metal salt, for example a sodium salt, or an alkaline earth metal salt, for example a magnesium salt, or a physiologically tolerable addition salt of an amine, these salts being especially important as soluble form in aqueous medium of the acids of formula I.

The present invention also relates to a process for the preparation of a compound of the general formula I or a salt thereof, which comprises reacting a derivative of an α-halogenated acid of the general formula X—$CR_1R_2$—COOR (III) in which X represents a halogen atom, e.g. Cl or Br, especially a bromine atom, and R, $R_1$ and $R_2$ have the meanings given above, with a diphenol of the general formula

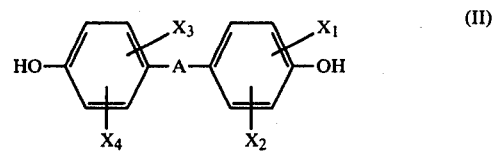

in which $X_1$, $X_2$, $X_3$, $X_4$ and A have the meanings given above, in the presence of a base, for example an alkali hydroxide, alkali carbonate, alkali alcoholate or sodium hydride.

Suitably the reaction is carried out in a solvent such, for example, as an alcohol, an aromatic hydrocarbon, a ketone, or a polar aprotic solvent, e.g. dimethylformamide or dimethylsulphoxide. For example, the sodium salt of compound II is reacted with compound III in an aromatic solvent, e.g. xylene, or compounds II and III are reacted in methyl ethyl ketone in the presence of an alkali metal carbonate.

A resulting compound of the general formula I or salt thereof may be converted to another compound of the general formula I or salt thereof. Thus, a resulting acid of the general formula I may then, if desired, be converted into a salt or into an ester; a resulting ester may be converted into another ester or into an acid; a resulting salt may also be converted into an acid.

For example, the condensation may be followed, when necessary, by the saponification, e.g. in a dilute alcoholic, especially alkaline, medium, of the ester obtained, especially by the action of base in aqueous or non-aqueous alcohol, or by the esterification of the acid of formula I; some esters of formula I are advantageously prepared by a transesterification reaction in an acidic or alkaline medium or by the action of an alcohol on the chloride of the acid of formula I.

A salt may be prepared, for example, by the action of an alkali hydroxide, e.g. alkali metal hydroxide, an alkaline earth metal salt or an amine on the acid of the general formula I suitably in solution in an alcohol or a ketone.

A substituted 4,4'-oxy or thio-diphenol starting material may be prepared by a conventional method from 4,4'-oxy or thio-diphenol, a known compound, for example by the action of chlorine or bromine on the diphenol in a solvent or, for an alkyl derivative, for example by the acylation of the benzene nuclei and then reducing the ketone obtained with hydrazine.

A 4,4'-sulphinyl or sulphonyl phenoxyalkane carboxylic acid may be prepared according to the invention by oxidation of the thio derivative, for example by hydrogen peroxide or even by substitution of a known 4,4'-sulphinyl or sulphonyl diphenol.

A compound of the general formula I may contain one or more asymmetric carbon atoms and is then usually in the form of a mixture of stereoisomers. The separation of the enantiomers (usually 3 enantiomers) may be effected by methods described in the literature. Accordingly, the names and formulae given herein are to be understood as including individual isomers as well as a mixture of isomers.

Compounds according to the invention were submitted to different pharmacological tests which showed in particular their importance as hypolipemic and uricosuric agents.

The $LD_{50}$ per os was measured in mice using the Bliss method [Quart. J. Pharm. Pharmacol. 2 192–216 (1938)] and was found to be more than 1,000 mg/kg. Thus the compounds tested have a low toxicity.

To investigate the hypocholesteremic activities of the compounds, tests were undertaken on mice which had received an injection of Triton and on mice which had not received this injection. The compounds under investigation (shown in Table I) were administered three times over a period of 48 hours in the doses specified in the Table.

The Table shows the percentage reduction in cholesterol level in the animals compared to animals which had not received the compounds to be tested. The results obtained show that the compounds of the invention possess a hypocholesteremic activity which is more significant in animals suffering from hypercholesteremia (Triton) that in normal animals, and that the minimum statistically active dosage can be less than 5 mg/kg. They also show that the hypocholesteremic activity of the acids is substantially the same as that of the corresponding esters. The results are compared with those of the known hypocholesteremic, clofibrate $LD_{50} = 1200$ mg/kg.

TABLE I

| Compound Example N° | Dose mg/kg | Hypocholesterolaemic activity | |
|---|---|---|---|
| | | Normal animals | Animals treated with Triton |
| 2 | 200 | −48%* | −54%* |
| 8 | 200 | −2.7% N.S. | −37.8%* |
| 9 | 100 | −64%* | −61%* |
| | 50 | −44%* | −51%* |
| | 25 | −20%* | −58%* |
| | 5 | −27% | −24%* |
| 10 | 50 | −43%* | −49%* |
| | 25 | −48%* | −46%* |
| | 5 | −19%* | −41%* |
| 13C | 200 | −19%* | −50%* |
| 18 | 200 | −25% | −55%* |
| | 100 | −19% | −53%* |
| | 50 | −3.8% N.S. | −43%* |
| 20 | 100 | −33%* | −70%* |
| | 50 | −21%* | −46%* |
| | 25 | −18% N.S. | −44%* |
| 33 | 100 | −47%* | −62%* |
| | 50 | −40%* | −53%* |
| | 25 | −18%* | −38%* |
| 34 | 100 | −43%* | −43%* |
| | 50 | −38%* | −23% N.S. |
| Clofibrate | 400 | −24%* | −23%* |

*result statistically significant P = 0.05
N.S. insignificant.

To investigate hypolipemic activity, 4,4′-oxy di(ethyl 2-phenoxyoctanoate) was administered orally to rats, twice a day for 4 days in the dosage specified in Table II. The changes in cholesterol, triglyceride and total lipid levels compared to controls were measured and the results shown below.

TABLE II

| | Plasmatic reductin in %* (compared to controls) | | |
|---|---|---|---|
| Unit dose | cholesterol | triglycerides | total lipids |
| 25 mg/kg | −37 | −70 | −47 |
| 10 mg/kg | −26 | −62 | −44 |
| 5 mg/kg | −20 | −45 | −37 |
| 1 mg/kg | −23 | −34 | −23 |

*statistically significant results P = 0.05

The uricosuric activity of compounds of the invention was demonstrated by the red phenol test in rats [H. C. Scarborough, G. R. McKinney—J. Med. Pharm. Chem. 5 175 (1962) and E. Kreppel—Med. Exptl. 1 285 (1959)]. Table III lists the results observed for some compounds representative of the invention as well as the results for benziodarone: 2-ethyl-3-benzofuranyl 4-hydroxy-3,5-diiodo-phenyl ketone, a uricosuric currently used in therapeutics.

TABLE III

| | | % of retention compared to control animals | | | |
|---|---|---|---|---|---|
| Compound | Dose mg/kg | after 15 minutes | after 30 minutes | after 45 minutes | after 60 minutes |
| Y | 100 | +22 | +32 | +50 | +41 |
| Z | 100 | +54 | +42 | +59 | +58 |
| benziodarone | 100 | +37 | +50 | +53 | −18* |

*statistically insignificant result
Y = 4,4′-oxy di(2-phenoxydodecanoic acid) (Example 34)
Z = 4,4′-oxy di(2-phenoxy undecanoic acid) (Example 33)

The derivatives of formula I and their pharmaceutically acceptable salts therefore possess hypolipemic, hypocholesterolemic and uricosuric properties and may be used as medicaments, in association with, or without, pharmaceutical carriers.

Accordingly, this invention also relates to a pharmaceutical composition which comprises a therapeutically effective amount of a compound of the formula I or a pharmaceutically acceptable salt thereof, and a pharmaceutical carrier therefor. Suitably, the pharmaceutical composition is in dosage unit form.

This invention also relates to the treatment of animals, especially mammals, more especially humans. The compounds of the invention may be administered to man, for example, orally, e.g. in the form of gelatin-coated pills or compressed tablets suitably in a dose ranging from 1 to 200 mg in the curative treatment of hypercholesterolemia, hypertriglyceridemia, hyperlipemia and arteriosclerosis, or as a preventative treatment for cardiac troubles.

The following examples serve to illustrate the invention but they are not intended to limit it thereto. Melting points were determined in a capillary tube (Gallenkamp apparatus).

EXAMPLE 1

4,4′-Thio di(ethyl 2-phenoxyoctanoate)

4.6 g of sodium were reacted with 100 ml of anhydrous ethanol and 21.8 g of 4,4′-thio diphenol were then introduced into the solution; after 15 minutes, 150 ml of xylene were poured into the medium and the ethanol was evaporated under reduced pressure. 50.1 g of 2-bromo ethyl octanoate were then introduced and the mixture maintained under reflux for 20 hours. Subsequently, the mixture was brought to 25° C., and 500 ml of water were introduced, the solution was separated in xylene, the aqueous phase extracted with ether, and the organic phases washed with an aqueous solution of 0.5N sodium hydroxide and then with water. After drying, the solvents were removed to obtain 42 g of ester in the form of an oil containing some traces of impurities. After column chromatography over a strongly alkaline anion exchange resin with aqueous ethanol (96%) as eluant, 38 g of pure ester were obtained. $n_D^{20} = 1.524$

EXAMPLE 2

4,4'-Thio di(2-phenoxy octanoic acid)

A solution of 30 g of 4,4'-thio di(ethyl 2-phenoxyoctanoate) in 100 ml of ethanol and 20 ml of aqueous sodium hydroxide (d=1.33) was brought to reflux and maintained at this temperature for a period of 10 hours. The solvent was removed and the residue dissolved in water and acidified by the addition of concentrated hydrochloric acid. The diacid was then taken up in diethyl ether. After drying the solution, the ether was evaporated and the fraction remaining crystallised from diisopropyl ether. After recrystallisation in dichloroethane, the diacid melted at 145° C.

EXAMPLE 3

4,4'-Oxy di(ethyl 2-phenoxy-2-methylpropionate)

20 g of 4,4'-oxy diphenol, 40 g of 2-bromo ethyl isobutyrate and 30 g of potassium carbonate in 200 ml of butan-2-one were brought to reflux and maintained at this temperature for 60 hours. The mineral products were then isolated and the butan-2-one removed by distillation. The residual oil was taken up in ether; the organic phase was washed with 1 N aqueous sodium hydroxide solution, and then with water. After drying and the removal of the ether, the residual oil was purified by column chromatography over an anion exchange resin at the same time washing out with aqueous ethanol (80%). In this manner 13 g of pure 4,4'-oxy di(ethyl 2-phenoxy-2-methylpropionate) were obtained in the form of oil. $n_D^{20} = 1.520$

EXAMPLE 4

4,4'-Oxy di(2-phenoxy-2-methyl propionic acid)

12 g of diester, obtained as in Example 3, were introduced into 50 ml of ethanol containing 2 g of sodium hydroxide. After refluxing for one hour, the solution was cooled, the precipitate which formed was dissolved in water, and the aqueous phase was acidified. After extraction in ether, drying of the solution and removal of the solvent, 10 g of 4,4'-oxy di(2-phenoxy-2-methyl propionic acid) were isolated in the form of a white precipitate. The product was purified by recrystallisation in benzene. In its pure state, it melted at 125° C.

EXAMPLE 5

4,4'-Oxy di(ethyl phenoxy acetate)

1.18 g of Na were reacted with 100 ml of ethanol and 5.2 g of 4,4'-oxy diphenol. 7.6 g of ethyl chloroacetate were then introduced. After refluxing for 5 hours, the solvent was evaporated, the residue was taken up in diethyl ether and the solution washed with an aqueous sodium hydroxide solution and then with water. 5.3 g of diester melting at 55° C. after recrystallisation in diisopropyl ether were obtained.

EXAMPLE 6

4,4'-Oxy di(phenoxy acetic acid)

The diester obtained in Example 5 was saponified in a dilute alcoholic medium.

3.5 g of diacid melting at 178° C. were obtained.

EXAMPLE 7

4,4'-Oxy di(ethyl 2-phenoxypropionate)

6.75 g of sodium hydride (80%) were introduced under a nitrogen atmosphere into a solution of 20.2 g of 4,4'-oxy diphenol in 250 ml of dimethylsulphoxide distilled over calcium hydride, and the mixture was heated at a temperature of 80° C. for one hour. After lowering the temperature to 25° C., 38.2 g of 2-bromo ethyl propionate were introduced drop by drop and then the medium was heated at 100° C. for 5 hours. The mixture was poured into 1 l of ice water, the solution was extracted twice with 300 ml of diethyl ether, the ether phase was washed with water and the solvent dried and evaporated: the residual oil was distilled under reduced pressure. 22 g of 4,4'-oxy di(ethyl 2-phenoxypropionate) were obtained. Boiling Point$_{10-2}$=236° C.; $n_D^{20}=1.519$.

EXAMPLE 8

4,4'-Oxy di(2-phenoxy propionic acid)

The ester of Example 7 was treated as described in Example 4; the diacid melting at 115° C. was obtained.

EXAMPLE 9

4,4'-Oxy di(ethyl 2-phenoxyoctanoate)

30 g of 4,4'-oxy diphenol were dissolved in 200 ml of anhydrous butan-2-one. After the addition of 15 g of potassium carbonte, 1 g of potassium iodide and 65 g of ethyl 2-bromooctanoate, the medium was heated at its reflux temperature for 17 hours. The solvent was filtered and evaporated, the residue taken up in diethyl ether and the organic phase washed with aqueous sodium hydroxide solution, then with water. After drying and removal of the ether, 69 g of oil were obtained which were purified by column chromatography using silica as adsorbent and and dichloroethane as eluant, or aluminium as adsorbent and cyclohexane as eluant. The diester, obtained in a yield of 91%, did not crystallise; $n_D^{20}=1.506$. The diester was also prepared using the method of operation described in Example 1, in a yield of 83%.

EXAMPLE 10

4,4'-Oxy di(2-phenoxy octanoic acid)

The saponification of the compound described in Example 9 may be carried out with sodium hydroxide or with potassium hydroxide in a dilute alcoholic medium as in Example 4, or even with potassium carbonate (or sodium carbonate) in an alcohol.

A solution of 23.5 g of diester in 100 ml of ethanol (96%) in the presence of 15 g of potassium carbonate was held at 95° C. for 10 hours. 2 parts of water were then introduced, the ethanol was evaporated and the mixture acidified by the addition of hydrochloric acid; the diacid was extracted with diethyl ether, the organic phase dried over magnesium sulphate or calcium sulphate and the solvent evaporated. 18.1 g of diacid were obtained which, after recrystallisation in dichloroethane, melted at 146°–7° C.

The disodium salt of this compound, prepared by the action of sodium hydroxide on the acid in solution in aqueous ethanol, formed a hydrate (½H$_2$O) and melted at more than 260° C.

The di(tri(hydroxymethyl)methyl amine) salt of this compound, prepared by the action of 2 mols of amine on a solution of the acid in butan-2-one, melted at 105° C.

EXAMPLE 11

4,4'-Oxy di(isopropyl 2-phenoxyoctanoate)

4.5 g of 4,4'-oxy di(2-phenoxy octanoic acid) were dissolved in 50 ml of benzene, and 2.8 g of thionyl chloride were then introduced. After refluxing for one hour, the solvent was evaporated and the residual oil dissolved in 40 ml of isopropanol. After stirring for three hours, the alcohol was evaporated and the residue was dissolved in chloroform. The organic solution was washed with an aqueous alkaline solution, then with water, and dried. The chloroform was removed and the residual oil then purified by chromatography over a column. 3.3 g of pure diester in the form of an oil were obtained.

EXAMPLE 12

4,4'-Oxy di(methyl 2-phenoxyoctanoate)

This compound was prepared in accordance with the method described in the preceding Example in a hield of 86%. It did not crystallise. $n_D^{20} = 1.1511$

EXAMPLE 13

4,4'-Oxy di[(2'-chloro)2-phenoxy octanoic acid and its ethyl ester]

A. 4,4'-Oxy di(2-chloro)phenol 20 g of 4,4'-oxy diphenol were introduced into 250 ml of methylene chloride, then, whilst maintaining the temperature of the medium at 5° C., 27 g of sulphuryl chloride were introduced. After 12 hours at room temperature, the mixture was poured on to 500 g of crushed ice. The organic solution was poured off, washed with water, dried and the solvent evaporated. After recrystallisation of the residue in benzene, 11 g of chlorinated diphenol melting at 115° C. were obtained.

B. 4,4'-Oxy di(ethyl(2'-chloro)2 phenoxyoctanoate)

This compound was prepared in a yield of 61% using the method described in Example 1; the result was an oil. $n_D^{20} = 1.518$

C. 4,4'-Oxy di[(2'-chloro)2-phenoxy octanoic acid]

The ester obtained according to (B) was hydrolysed with potassium hydroxide in a dilute alcoholic medium. After recrystallisation in cyclohexane, the pure acid melted at 86° C.

EXAMPLE 14

4,4'-Oxy di[ethyl(2',6'-dichloro)2-phenoxy octanoate]

A. 4,4'-Oxy di(2,6-dichloro)phenol 40 g of 4,4'-oxy diphenol were suspended in 400 ml of anhydrous 1,2-dichloroethane and 65 ml of sulphuryl chloride were slowly introduced into the medium. At the end of the addition, the solution was brought to reflux; this was maintained for 14 hours. A part of the solvent was then removed under reduced pressure, the mixture was cooled to −30° C. and the precipitate which formed was filtered. The precipitate was recrystallised in carbon tetrachloride. The pure product melted at 150° C.

B. 4,4'-Oxy di[ethyl(2,6-dichloro)2-phenoxy octanoate]

This compound was prepared in a yield of 90% using the method described in Example 9. The result was an oil. $n_D^{20} = 1.526$

EXAMPLE 15

4,4'-Oxy di[ethyl(2'-bromo)2-phenoxy octanoate]

A. 4,4'-Oxy di(2-bromo phenol)

32 g of bromine were introduced over 2½ hours into a suspension of 20 g of 4,4'-oxy diphenol in 150 ml of anhydrous methylene chloride. The mixture was then hydrolysed over crushed ice. The end product was extracted in diethyl ether, then recrystallised in benzene and cyclohexane. The pure product, melting at 106° C., was obtained in a yield of 35%.

B. 4,4'-Oxy di[ethyl(2'-bromo)2-phenoxy octanoate]

This compound was prepared in a yield of 70% using the method described in Example 9. The result was an oil. $n_D^{20} = 1.522$

EXAMPLES 16 to 38

The compounds of the invention shown in the following Table were prepared using the methods set out above.

(see Table on following pages)

| Example No | Formula | Physical Constant |
|---|---|---|
| | $H_5C_2OOC-CH(R_2)-O-C_6H_4-O-C_6H_4-O-CH(R_2)-COOC_2H_5$ | |
| 16 | $R_2 = CH_2-CH_3$ | oil B.Pt. = 210° C. (2 × 10$^{-2}$) |
| 17 | $R_2 = (CH_2)_2-CH_3$ | oil B.Pt. = 220° C. (5 × 10$^{-2}$) |
| 18 | $R_2 = (CH_2)_3-CH_3$ | oil B.Pt. = 240° C. (2 × 10$^{-2}$) |
| 19 | $R_2 = (CH_2)_4-CH_3$ | oil $n_D^{20} = 1.508$ |
| 20 | $R_2 = (CH_2)_6-CH_3$ | oil $n_D^{20} = 1.494$ |
| 21 | $R_2 = (CH_2)_7-CH_3$ | oil $n_D^{20} = 1.498$ |

-continued

| Example No | Formula | Physical Constant |
|---|---|---|
| 22 | $R_2 = (CH_2)_8—CH_3$ | oil $n_D^{20} = 1.495$ |
| 23 | $R_2 = (CH_2)_9—CH_3$ | oil $n_D^{20} = 1.489$ |
| 24 | $H_5C_2OOC—\underset{\underset{CH_3—(CH_2)_5}{\mid}}{CH}—O—\phenyl—SO—\phenyl—O—\underset{\underset{(CH_2)_5—CH_3}{\mid}}{CH}—COOC_2H_5$ | oil $n_D^{20} = 1.525$ |
| 25 | $H_5C_2OOC—\underset{\underset{CH_3—(CH_2)_5}{\mid}}{CH}—O—\phenyl—SO_2—\phenyl—O—\underset{\underset{(CH_2)_5—CH_3}{\mid}}{CH}—COOC_2H_5$ | oil $n_D^{20} = 1.521$ |
|  | $HOOC—\underset{\underset{R_2}{\mid}}{CH}—O—\phenyl—O—\phenyl—O—\underset{\underset{R_2}{\mid}}{CH}—COOH$ | M.Pt. = 164° C. |
| 26 | $R_2 = CH_2—CH_3$ | M.Pt. = 164° C. |
| 27 | $R_2 = (CH_2)_2—CH_3$ | M.Pt. = 102° C. |
| 28 | $R_2 = (CH_2)_3—CH_3$ | M.Pt. = 126° C. |
| 29 | $R_2 = CH_2—CH(CH_3)_2$ | M.Pt. = 121° C. |
| 30 | $R_2 = (CH_2)_4—CH_3$ | M.Pt. = 126° C. |
| 31 | $R_2 = (CH_2)_6—CH_3$ | M.Pt. = 92° C. |
| 32 | $R_2 = (CH_2)_7—CH_3$ | M.Pt. = 110° C. |
| 33 | $R_2 = (CH_2)_8—CH_3$ | M.Pt. = 90° C. |
| 34 | $R_2 = (CH_2)_9—CH_3$ | M.Pt. = 94° C. |
| 35 | $HOOC—\underset{\underset{CH_3—(CH_2)_5}{\mid}}{CH}—O—\underset{Cl}{\overset{Cl}{\phenyl}}—O—\underset{Cl}{\overset{Cl}{\phenyl}}—O—\underset{\underset{(CH_2)_5—CH_3}{\mid}}{CH}—COOH$ | M.Pt. = 110° C. |
| 36 | $HOOC—\underset{\underset{CH_3—(CH_2)_5}{\mid}}{CH}—O—\overset{Br}{\phenyl}—O—\overset{Br}{\phenyl}—O—\underset{\underset{(CH_2)_5—CH_3}{\mid}}{CH}—COOH$ | M.Pt. = 96° C. |
| 37 | $HOOC—\underset{\underset{CH_3—(CH_2)_5}{\mid}}{CH}—O—\phenyl—\underset{\underset{O}{\parallel}}{S}—\phenyl—O—\underset{\underset{(CH_2)_5—CH_3}{\mid}}{CH}—COOH$ | M.Pt. = <40° C. rf* = 0.19 |
| 38 | $HOOC—\underset{\underset{CH_3—(CH_2)_5}{\mid}}{CH}—O—\phenyl—SO_2—\phenyl—O—\underset{\underset{(CH_2)_5—CH_3}{\mid}}{CH}—COOH$ | M.Pt. = <40° C. rf* = 0.24 |

*The chromatography of the compounds of Examples 37 and 38 is carried out on plates of silica gel 60F254 (MERCK) (thickness 0.25 mm). The eluant is toluene/ethylformiate/formic acid in a ratio by volume 50:45:5. Under these conditions, the rfs of 4,4'-sulphinyl diphenol and 4,4'-sulphonyl diphenol are respectively 0.12 and 0.16.

We claim:

1. A compound of the formula

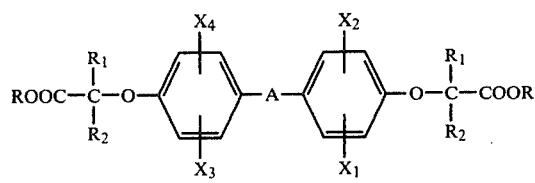

wherein
R is hydrogen or alkyl of 1 to 5 carbon atoms,
$R_1$ is hydrogen or alkyl of 1 to 3 carbon atoms,
$R_2$ is alkyl of 4 to 12 carbon atoms,
A is O, S, SO or $SO_2$; and each of $X_1$, $X_2$, $X_3$ and $X_4$ is independently hydrogen, halogen or alkyl of 1 to 3 carbon atoms or a pharmaceutically acceptable salt thereof.

2. A compound as claimed in claim 1, wherein R represents hydrogen.

3. A compound as claimed in claim 1, wherein R represents alkyl of 1 to 5 carbon atoms.

4. A compound as claimed in claim 1, which is 4,4'-oxy di(ethyl 2-phenoxyoctanoate).

5. A compound as claimed in claim 1, which is selected from 4,4'-oxy di(2-phenoxy octanoic acid) and its pharmaceutically acceptable salts.

6. A compound as claimed in claim 1, which is selected from 4,4'-thio di(2-phenoxy octanoic acid) and its esters and its pharmaceutically acceptable salts.

7. A compound as claimed in claim 1, which is 4,4'-oxy di(ethyl 2-phenoxynonanoate).

8. A compound as claimed in claim 1, which is selected from 4,4'-oxy di(2-phenoxy undecanoic acid) and its pharmaceutically acceptable salts.

9. A pharmaceutical composition in dosage unit form for treatment of an animal against hypercholoesterolemia, hypertiglyceridemia, hyperlipemia or arteriosclorosis comprising an amount effective to combat said hypercholoesterolemia, hypertiglyceridemia, hyperlipemia or arterioschlorosis of a compound of the formula

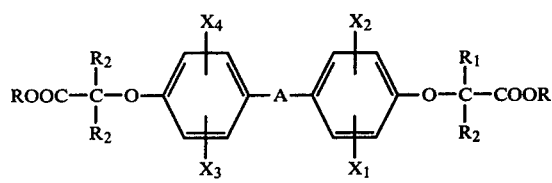

wherein
R is hydrogen or alkyl of 1 to 5 carbon atoms,
$R_1$ is hydrogen or alkyl of 1 to 3 carbon atoms,
$R_2$ is hydrogen or alkyl of 1 to 12 carbon atoms,
A is selected from the group consisting of O, S, SO, and $SO_2$, and
$X_1$, $X_2$, $X_3$ and $X_4$ are each independently selected from the group consisting of hydrogen, halogen, and alkyl of 1 to 3 carbon atoms, or a pharmaceutically acceptable salt thereof, and a pharmaceutical carrier therefor.

10. The pharmaceutical composition of claim 9 wherein $R_2$ is an alkyl of 1 to 12 carbon atoms.

11. The pharmaceutical composition of claim 9 which contains from 1 to 200 mg of active ingredient per dosage unit.

12. A composition of claim 9 wherein said dosage unit is a tablet.

13. A composition of claim 9 wherein said dosage unit is a gelatin-coated pill.

14. A method of treating a human against hypercholesterolemia, hypertriglyceridemia, hyperlipemia and arteriosclerosis, wherein there is administered to the human a pharmaceutically acceptable amount of a compound of the formula

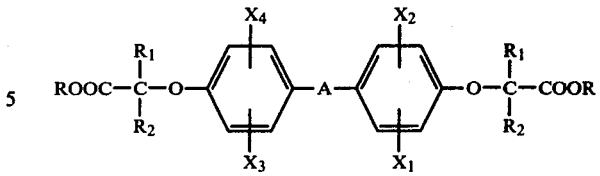

wherein
R is hydrogen or alkyl of 1 to 5 carbon atoms,
$R_1$ is hydrogen or alkly of 1 to 3 carbon atoms,
$R_2$ is hydrogen or alkyl of 1 to 12 carbon atoms,
A is selected from the group consisting of O, S, SO, and $SO_2$, and
$X_1$, $X_2$, $X_3$, and $X_4$ are each independently selected from the group consisting of hydrogen, halogen, and alkyl of 1 to 3 carbon atoms, or a pharmaceutically acceptable salt thereof.

15. The method of claim 14 wherein $R_2$ is alkyl of 1 to 12 carbon atoms.

16. A method as claimed in claim 14, wherein there is administered from 1 to 200 mg of active ingredient.

17. A method of maintaining or decreasing uric acid levels of the body which comprises administering to a patient in need thereof a uricosically effective amount in unit dosage form of a compound of the formula

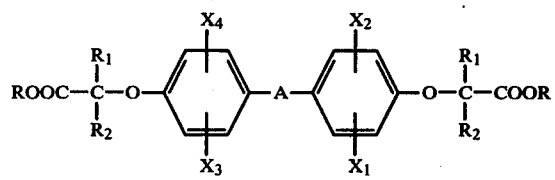

wherein
R is hydrogen or alkyl of 1 to 5 carbon atoms,
$R_1$ is hydrogen or alkyl of 1 to 3 carbon atoms,
$R_2$ is hydrogen or alkyl of 1 to 12 carbon atoms,
A is selected from the group consisting of O, S, SO, and $SO_2$, and
$X_1$, $X_2$, $X_3$, and $X_4$ are each independently selected from the group consisting of hydrogen, halogen, and alkyl of 1 to 3 carbon atoms.

18. The method of claim 17 wherein $R_2$ is alkyl of 1 to 12 carbon atoms.

* * * * *